(12) United States Patent
Staniforth et al.

(10) Patent No.: US 7,754,240 B2
(45) Date of Patent: Jul. 13, 2010

(54) TOPICAL PHARMACEUTICAL FORMULATIONS AND METHODS OF TREATMENT

(75) Inventors: John Nicholas Staniforth, Bath (GB); Michael John Tobyn, Wiltshire (GB)

(73) Assignee: Pharmakodex Limited, Wiltshire (GB)

( * ) Notice: Subject to any disclaimer, the term of this patent is extended or adjusted under 35 U.S.C. 154(b) by 1059 days.

(21) Appl. No.: 10/312,475

(22) PCT Filed: Jun. 26, 2001

(86) PCT No.: PCT/GB01/02823

§ 371 (c)(1),
(2), (4) Date: Dec. 23, 2002

(87) PCT Pub. No.: WO02/00203

PCT Pub. Date: Jan. 3, 2002

(65) Prior Publication Data

US 2003/0138503 A1    Jul. 24, 2003

(30) Foreign Application Priority Data

Jun. 26, 2000    (GB) .................................. 0015617.4

(51) Int. Cl.
*A61K 9/144* (2006.01)
(52) U.S. Cl. ...................... 424/484; 424/400
(58) Field of Classification Search .................. None
See application file for complete search history.

(56) References Cited

U.S. PATENT DOCUMENTS

| | | | |
|---|---|---|---|
| 4,091,090 A * | 5/1978 | Sipos | 424/45 |
| 4,151,274 A | 4/1979 | Schlueter et al. | 424/80 |
| 4,278,679 A | 7/1981 | Madison et al. | |
| 4,369,784 A | 1/1983 | de Buman et al. | 128/271 |
| 4,765,986 A | 8/1988 | Liedtke | 424/449 |
| 4,892,890 A | 1/1990 | Damani | 514/784 |
| 5,121,158 A * | 6/1992 | Chen et al. | 355/35 |
| 5,208,035 A * | 5/1993 | Okuyama et al. | 424/446 |
| 5,308,343 A | 5/1994 | Gafner | 604/289 |
| 5,389,686 A | 2/1995 | Diop et al. | |
| 5,474,783 A * | 12/1995 | Miranda et al. | 424/448 |
| 5,597,849 A | 1/1997 | McGinity et al. | 514/648 |
| 5,863,941 A | 1/1999 | Liedtke | 514/555 |
| 5,968,544 A | 10/1999 | Howard et al. | |

FOREIGN PATENT DOCUMENTS

| | | | |
|---|---|---|---|
| AU | B-47036 | * | 5/1990 |
| WO | WO 8912480 | | 6/1989 |

OTHER PUBLICATIONS

Remington's Pharmaceutical Sciences, 17th Edition, (1985) pp. 773-791.
Remington's Pharmaceutical Sciences, 17th Edition, (1985) pp. 1054-1058.

* cited by examiner

*Primary Examiner*—Eric E. Silverman
(74) *Attorney, Agent, or Firm*—Davidson, Davidson & Kappel, LLC

(57) ABSTRACT

In certain embodiments, the present invention is directed to a pharmaceutical formulation for topical administration on a mammal, comprising a unit dose of a therapeutically effective amount of a therapeutic agent and a pharmaceutically acceptable carrier medium therefor, said formulation being solid at ambient temperature and having a softening point of not higher than 35° C., such that when the formulation is placed in continuous contact with the skin of a mammalian patient, it is softened to a consistency to effect substantial application of the unit dose of said therapeutic agent onto a desired skin area of the mammalian patient within a time period of less than 10 minutes.

46 Claims, No Drawings

TOPICAL PHARMACEUTICAL FORMULATIONS AND METHODS OF TREATMENT

The present invention relates to pharmaceutical formulations for dermal administration of therapeutic agents to an animal patient, pharmaceutical products containing the same and methods of treatment employing such pharmaceutical formulations and products.

In the treatment of localised disorders, such as skin infections or the like, it has often been desirable to prescribe therapeutic agents in a form that has a topical, or localised effect. Topical formulations have been available in a variety of forms, including creams, ointments, solutions, lotions, suspensions, pastes, emulsions, foams and the like. Water miscible creams have generally been employed for moist or weeping lesions, whereas ointments have been generally chosen for dry, lichenified or scaly lesions or where a more occlusive effect has been required. Lotions have generally been useful when minimal application to a large or hair-bearing area has been required or for the treatment of exudative lesions.

It is important with any dosing regime, that accurate dosing is achieved and in the case of topical formulations substantially as hereinbefore described it is particularly important that patients follow the instructions carefully and thus avoid any adverse effects. For example, with such topical formulations a higher dose than recommended could easily be accidentally achieved, typically due to difficulties of knowing the precise amount of formulation necessary for application.

Suitable quantities of topical formulations hitherto prescribed for specific areas of the body have been as follows:

|  | Creams and ointments (g) | Lotions (mL) |
| --- | --- | --- |
| Face | 15 to 30 | 100 |
| Both hands | 25 to 50 | 200 |
| Scalp | 50 to 100 | 200 |
| Both arms or both legs | 100 to 200 | 200 |
| Trunk | 400 | 500 |
| Groins and genitalia | 15 to 25 | 100 |

The above amounts have usually been suitable for an adult for twice daily application for one week. However, the above recommendations have not been applicable for all topical formulations and a number of categories of topical formulations require specialised dosing regimes. For example, the above recommendations have not been applicable for corticosteroid preparations. More particularly, for potent corticosteroid formulations, more care has been required for application as absorption through the skin can cause severe pituitary-adrenal-axis suppression and Cushing's syndrome, both of which depend on the area of the body treated and the duration of the treatment. Corticosteroid preparations have, therefore, normally been applied once or twice daily (it has not been necessary to apply them more frequently) and suitable quantities hitherto prescribed for specific areas of the body have been as follows:

|  | Creams and ointments (g) |
| --- | --- |
| Face and neck | 15 to 30 |
| Both hands | 15 to 30 |
| Scalp | 15 to 30 |
| Both arms | 30 to 60 |
| Both legs | 100 |
| Trunk | 100 |
| Groins and genitalia | 15 to 30 |

Furthermore, treatment of severe atopic eczema on the limbs or body (or a flare-up of mild to moderate eczema) has often required still further consideration. For example, treatment has in some cases required application of a potent or moderately potent corticosteroid for the first one to two weeks, followed by a weaker preparation as the condition improves; an emollient has also been used.

It will be appreciated from the above that considerable care is required in following a dosing regime for topical formulations and a particular consideration that should be taken into account is the maximum dosage that can be tolerated for any therapeutic agent during a treatment course. For example, the following are specific examples of prior art topical formulations where specific dosing regimes, and in particular maximum dosages, have been instructed. Examples are:

Doxepin Hydrochloride, recommended to be applied thinly three to four times daily, typically with a maximum 3 g administration per application, a typical daily maximum administration of 12 g and suitably coverage should be less than about 10% of body surface;

Clobetasol Propionate, recommended to be applied thinly one to two times daily for up to four weeks, typically with a maximum administration of about 50 g of a 0.05% preparation per week; and Diflucortolone Valerate, recommended to be applied one to two times daily for up to four weeks (0.1% preparation) or two weeks (0.3% preparation), with typically a maximum administration of about 60 g of a 0.3% preparation per week.

In particular, it has been seen to be especially important for topical formulations of Calcipotriol, that the maximum dosage should be monitored. For example, there has been seen to be a risk of hypercalcemia if the recommended maximum weekly dose of Calcipotriol has been exceeded. Unfortunately, the above has not always been clearly explained in patient information provided with topical formulations of Calcipotriol. For example, topical formulation of Calcipotriol available under the trade mark Dovonex have advised liberal application despite the above described potential for hypercalcaemia, and as can be appreciated, therefore, the above can be problematic. The recommended dosing regime for a topical formulation of Calcipotriol, however, has been to apply once or twice daily, with a maximum weekly dose of 100 g. For patients over six years, the formulation should be applied twice daily; for patients from six to twelve years, a maximum weekly dose of 50 g; and for patients over twelve years, a maximum weekly dose of 75 g.

To alleviate problems encountered with treatment regimes where it has been important to observe a maximum dosage of a therapeutic agent for dermal administration, it would be beneficial to be able to provide means for substantially accurately dermally administering such a therapeutic agent to a patient. Such accurate administration should obviate the detrimental side effects that have hitherto been observed when maximum dosages have been exceeded.

A difficulty that has, in the past, been encountered when trying to achieve the above described accurate administration, has been where a therapeutic agent has been applied to the skin in a topical formulation, and it has often been a problem for a patient to be able to measure out a precise amount of such a topical formulation. It has, therefore, been especially difficult to ensure that the patient has received an accurate dosing of the therapeutic agent. One method of metering, or dosing, the amount of a therapeutic agent applied to a patient's skin in such a topical formulation has been for a patient to squeeze such a topical formulation from a dispenser, such as a tube, along an index finger starting at the fingertip down to the first joint and the amount of therapeutic agent thus to be administered has been known as the fingertip unit (FTU). One FTU generally approximates to about 500 mg of a topical formulation and is generally sufficient to cover an area that is twice that of a flat adult hand. Such administration has not, however, hitherto achieved accurate dosing, and in particular the above is. problematic in that the FTU is only an approximate unit and its magnitude varies from patient to patient.

It has also been known to deliver therapeutic agents transdermally by applying to the skin of a patient an adhesive patch containing a therapeutic agent. Such patches have typically further included a rate-moderating membrane, an adhesive, a liner and a backing material. The adhesive has often required special formulation to ensure compatibility with the other components of such patches and this type of formulation has often increased the cost of such patches. Furthermore, not all therapeutic agents are suitable for inclusion in such patches (typically therapeutic agents having a localised therapeutic effect have not hitherto been employed in such patches) and the use of such patches has not, therefore, offered a possible route of dermal administration for such therapeutic agents.

Such patches have also been referred to in the pharmaceutical field as "medicinal plasters". For example, U.S. Pat. No. 4,765,986 describes a medicinal plaster which comprises a drug present in a carrier substance and the carrier substance is affixed to a porous and flexible synthetic material U.S. Pat. No. 5,863,941 is also concerned with dermal administration of therapeutic agents and in particular describes a method of treating pathological symptoms of the inner ear. More particularly, U.S. Pat. No. 5,863,941 describes the use of a carrier substance and a therapeutic agent, the latter comprising a local anaesthetic present in an amount of about 0.5 to 40% by weight of the carrier substance. The carrier substance and therapeutic agent described in U.S. Pat. No. 5,863,941 for use in the treatment of the inner ear, may take the form described in U.S. Pat. No. 4,765,986

For dermal administration of therapeutic agents suitable for provision in liquid form, EP0375763B describes an applicator device for dosing a liquid, such as a medicinal solution, onto the skin of a patient. The device described by EP0375763B includes a micrometric screw dosing mechanism which allows variation of the internal cavity thereof. An applicator device of the type described in EP0375763B, however, is of course, only suitable for use with therapeutic agents that can be provided in solution.

The present invention is an improvement the prior art and provides pharmaceutical formulations suitable for dermally administering one or more therapeutic agents to an animal patient, pharmaceutical products containing the same, processes of preparing such pharmaceutical formulations and products, and methods of treating an animal patient employing such pharmaceutical formulations and products. In particular, the present invention provides pharmaceutical formulations, pharmaceutical products containing the same, processes of preparing such formulations and products, and methods of treatment, which each allow accurate dosing of one or more therapeutic agents to the skin of an animal patient.

In certain embodiments, the present invention is directed to a pharmaceutical formulation for topical administration on a mammal, comprising a unit dose of a therapeutically effective amount of a therapeutic agent and a pharmaceutically acceptable carrier medium therefor, said formulation being solid at ambient temperature and having a softening point of not higher than 35° C., such that when the formulation is placed in continuous contact with the skin of a mammalian patient, it is softened to a consistency to effect substantial application of the unit dose of said therapeutic agent onto a desired skin area of the mammalian patient within a time period of less than 10 minutes.

Certain embodiments of the present invention are directed to a pharmaceutical formulation for topical administration on a mammal, comprising a unit dose of a therapeutically effective amount of a therapeutic agent and a pharmaceutically acceptable carrier medium therefor, said formulation having a softening point of not higher than skin temperature of a mammalian patient, said formulation having an aspect ratio (wall:face) of less than 1:1.

Certain embodiments are directed to a pharmaceutical formulation for topical administration on a mammal, comprising a unit dose of a therapeutically effective amount of a therapeutic agent and a pharmaceutically acceptable carrier medium therefor, said formulation upon being placed in continuous contact with the skin of a mammalian patient being softened to a consistency to effect substantial application of the unit dose of said therapeutic agent onto a desired skin area of the mammalian patient within a time period of less than 10 minutes.

Certain embodiments are directed to a pharmaceutical formulation for topical administration on a mammal, comprising a compacted granulate of a unit dose of a therapeutic agent and a pharmaceutically acceptable carrier medium therefor, said compacted granulate having a softening point of not higher than skin temperature of a mammalian patient.

In certain embodiments, the formulation has a shape to facilitate the topical administration of the drug. For example, the formulation can have at least one surface which is flat; at least one concave surface; at least one convex surface; two flat surfaces; two concave surfaces or two convex surfaces. The shape of the formulation can be in the form of a standard tablet, spherical or half-spherical. Bullet shaped and conical shaped formulations are not preferred in the present invention.

In preferred embodiments, the formulations of the present invention have a total weight from about 50 mg to less than 1 g. preferably from about 100 mg to about 900 mg and more preferably from about 250 mg to about 750 mg. The formulations of the present invention can be higher than 1 gram if desired.

In formulations which are prepared for human patients, the dosage form has a softening point not higher than the normal external temperature (skin temperature) of a human. This temperature is typically not higher than about 35° C. In certain embodiments, the formulation has a softening point from about 30° C. to not higher than 35° C.

Certain embodiments are directed to a pharmaceutical formulation containing a unit dose of at least one therapeutic agent suitable for topical administration to an mammalian patient, said formulation being a solid during final manufacture, and having prior to application to an area of skin of said mammalian patient a spreading consistency suitable for application to said area of skin, said formulation being individually contained in a plastic container having a removable or breakable enclosure for dispensing said unit dose.

In certain embodiments, the dosage form can be a plurality of substantially discrete substantially solid particles comprising a therapeutic agent admixed with a pharmaceutically acceptable carrier medium, said particles having a softening point form about 30° C. to about 35° C. The particles can be enclosed in a satchet, a capsule or a device suitable to dispense a unit dose of the particles.

In certain embodiments, the invention is directed to a process of preparing a pharmaceutical formulation for dermal administration to an animal patient, the pharmaceutical formulation containing a unit dose of at least one therapeutic agent, which process comprises:
(a) admixing the at least one therapeutic agent with a carrier medium therefor so as to obtain a mixture thereof; and
(b) shaping at least a portion of the mixture obtained by step (a) to obtain a solid shaped formulation having an aspect ratio (wall:face) of less than 1:1, said resultant pharmaceutical formulation having a softening print of not higher than the skin temperature of a mammal, said formulation upon being placed in continuous contact with the skin of a mammalian patient being softened to a consistency to effect substantial application of the unit dose of said therapeutic agent onto a desired skin area of the mammalian patient within a time period of less than 10 minutes.

Other embodiments are directed to a process of preparing a pharmaceutical formulation for effecting topical administration of at least one therapeutic agent suitable for topical administration to a mammalian patient, the pharmaceutical formulation containing a unit dose of the therapeutic agent and having a substantially solid dosage form at ambient temperature and being softenable, on application thereof to an area of skin of said mammalian patient, to a consistency that can be absorbed by the area of skin so as to effect administration of the unit dose of the therapeutic agent to said mammalian patient, the process comprising, in the order specified, the steps of:
(a) admixing at least one therapeutic agent suitable for topical or administration to a mammalian patient and at least one ingredient suitable for providing a carrier medium therefor so as to obtain a mixture thereof;
(b) cooling the mixture obtained by step (a) so as to effect substantial solidification thereof; and
(c) shaping at least a portion of the substantially solidified mixture obtained by step (b) to provide a substantially solid dosage form containing a unit dose of the at least one therapeutic agent.

Other embodiments are directed to a process of preparing a unit dose of a topical pharmaceutical formulation, comprising suitable for dermal administration to a mammalian patient:
(a) admixing a therapeutic agent with at least one pharmaceutically acceptable carrier medium therefor so as to obtain a mixture thereof;
(b) cooling the mixture obtained in step (a) to a temperature of not higher than about 15° C.; the cooled mixture obtained by step (b) to obtain a semi-solid unit dose of said therapeutic agent, said formulation having, at ambient temperature prior to application to an area of skin of an animal patient, a spreading consistency suitable for application to the area of skin of the animal patient.

There is provided by the present invention, therefore, a process of preparing a pharmaceutical formulation, containing a unit dose of at least one therapeutic agent, which formulation is for dermal administration to an animal patient, which process comprises:
(a) admixing the at least one therapeutic agent with a carrier medium therefor so as to obtain a mixture thereof; and
(b) shaping at least a portion of the mixture obtained by step (a), so as to obtain said pharmaceutical formulation.

More particularly, there is provided by the present invention, a process of preparing a pharmaceutical formulation for effecting dermal administration of at least one therapeutic agent suitable for dermal administration to an animal patient, which pharmaceutical formulation contains a unit dose of the at least one therapeutic agent, which process comprises:
(a) admixing the at least one therapeutic agent with a carrier medium therefor so as to obtain a mixture thereof; and
(b) shaping at least a portion of the mixture obtained by step (a), which shaping comprises tableting at least a portion of the mixture obtained by step (a) so as to provide a pharmaceutical formulation containing a unit dose of the at least one therapeutic agent.

There is also provided by a first aspect of the present invention a process of preparing a pharmaceutical formulation for effecting dermal administration of at least one therapeutic agent suitable for dermal administration to an animal patient, the pharmaceutical formulation typically having a substantially solid dosage form at ambient temperature and having a softening point substantially as hereinafter described in greater detail of not higher than skin temperature of an animal patient, which pharmaceutical formulation contains a unit dose of the at least one therapeutic agent, which process comprises:
(a) admixing the at least one therapeutic agent with a major proportion of a carrier medium therefor so as to obtain a mixture thereof, the carrier medium having a softening point not higher than skin temperature of an animal patient; and
(b) shaping at least a portion of the mixture obtained by step (a) at a temperature below the softening point of the carrier medium, to form a substantially solid form (typically a substantially solid dosage form) having a softening point of not higher than skin temperature of an animal patient and containing a unit dose of the at least one therapeutic agent.

Shaping a mixture of the at least one therapeutic agent and carrier medium substantially as hereinbefore described typically comprises tableting at least a portion of the mixture obtained by any step (a) substantially as hereinbefore described so as to provide a pharmaceutical formulation containing a unit dose of the therapeutic agent. Typically "tableting" as described herein can comprise introducing, at least a portion of a mixture of the at least one therapeutic agent and a carrier medium prepared according to the present invention, into a tableting press and compressing the introduced mixture to yield a substantially solid form, typically a substantially solid dosage form having a size and configuration suitable for dermally administering the at least one therapeutic agent substantially as herein described to an animal patient. Indeed, tablets containing therapeutic agents, as already forming part of the state of the art, are a common form of medicinal preparation for oral delivery and are made by compression of a mixture of finely divided ingredients and are known to be advantageous in view of their relative precision and reproducibility of dose, their desirable handling properties and generally relatively inexpensive processes of manufacture. Tablets according to the present invention for effecting dermal administration of a unit dose of at least one therapeutic agent to an animal patient do not, however, form part of the state of the art but do similarly possess the advantages associated with known tablets for oral administration substantially as hereinbefore described.

A process of preparing a pharmaceutical formulation according to the present invention may further comprise cooling at least a portion of a mixture of the at least one therapeutic agent and carrier medium therefor prepared substantially as hereinbefore described, which cooling can improve handling properties of the mixture and may also increase the speed of tableting as carried out according to the present invention. Suitably cooling may be carried out prior to and/or during shaping of a mixture of the at least one therapeutic agent and a carrier medium therefor as prepared according to the present invention substantially as hereinbefore described. Preferably, the mixture can be cooled to a temperature of not more than about 15° C., advantageously not more than about 10° C., for example, not more than about 0° C., prior to, and/or during shaping substantially as hereinbefore described.

Suitably, cooling as carried out in a process according to the present invention may be effected at least in part by using a cooled tableting press. Advantageously, a mixture of the at least one therapeutic agent and carrier medium therefor can also be cooled prior to introduction thereof into such a tableting press.

In a preferred process according to the first aspect of the present invention there is provided a process of preparing a pharmaceutical formulation for effecting dermal administration of at least one therapeutic agent suitable for dermal administration to an animal patient, the pharmaceutical formulation containing a unit dose of the at least one therapeutic agent and having a substantially solid dosage form at ambient temperature and being softenable, on application thereof to an area of skin of an animal patient, to a consistency that can be absorbed by the area of skin so as to effect administration of the unit dose of the therapeutic agent to the animal patient, which process comprises, in the order specified, the steps of:
(a) admixing at least one therapeutic agent suitable for dermal administration to an animal patient and at least one ingredient suitable for providing a carrier medium therefor so as to obtain a mixture thereof;
(b) cooling (preferably at a temperature of less than about 10° C., preferably less than about 0° C.) the mixture obtained by step (a) so as to effect substantial solidification thereof; and
(c) shaping at least a portion of the substantially solidified mixture obtained by step (b) to provide a substantially solid form (typically a substantially solid dosage form) of a pharmaceutical formulation according to the first aspect of the present invention.

Typically a process according to the first aspect of the present invention further comprises a step of reducing particle size (such as by granulating, prilling or the like) prior to shaping to a substantially solid dosage form. Suitably the substantially solidified mixture obtained by step (b) above, can be granulated to provide a plurality of particles having a particle size in the range of 100 to 1000 microns.

It may be preferred that a pharmaceutical formulation as provided by the present invention is substantially free of preservatives substantially as hereinafter described in greater detail and in such cases it is preferred that a process according to the present invention is carried out under aseptic conditions.

It may also be preferred that a pharmaceutical formulation as provided by the present invention is substantially free of antioxidants substantially as hereinafter described in greater detail and in such cases it is preferred that, where a process according to the present invention includes packaging of the pharmaceutical formulation, at least such packaging is carried out in a substantially inert atmosphere, such as nitrogen or the like.

There is also provided by the present invention a pharmaceutical formulation comprising a unit dose of at least one therapeutic agent and a carrier medium therefor, which pharmaceutical formulation is capable of effecting dermal administration of the unit dose of the at least one therapeutic agent to an animal patient.

According to the above described first aspect of the present invention there is further provided a pharmaceutical formulation for effecting dermal administration of at least one therapeutic agent suitable for dermal administration to an animal patient, which pharmaceutical formulation has a substantially solid dosage form at ambient temperature and has a softening point (substantially as hereinafter described in greater detail) of not higher than skin temperature of an animal patient, and contains a unit dose of at least one therapeutic agent suitable for dermal administration to an animal patient.

More particularly, according to the above described first aspect of the present invention there is provided a pharmaceutical formulation for effecting dermal administration of at least one therapeutic agent suitable for dermal administration to an animal patient, which formulation has a substantially solid dosage form at ambient temperature and comprises a unit dose of the at least one therapeutic agent in admixture with a carrier medium therefor, the formulation being characterised by the solid dosage form being softenable on application thereof to an area of skin of an animal patient, whereby following application to the area of skin the solid dosage form is softened to a consistency that can be substantially absorbed by the area of skin so as to effect administration of the unit dose of the therapeutic agent to the animal patient.

Even more particularly, there is provided by the above described first aspect of the present invention a pharmaceutical formulation for effecting dermal administration of at least one therapeutic agent suitable for dermal administration to an animal patient, which formulation has a substantially solid dosage form at ambient temperature and comprises a unit dose of the at least one therapeutic agent in admixture with a carrier medium therefor, the formulation being characterised by the substantially solid dosage form being softenable on application thereof to an area of skin of an animal patient, whereby following application to the area of skin the solid dosage form is softened to a consistency that can be substantially completely absorbed by the area of skin so as to effect substantially complete administration of the unit dose of the therapeutic agent to the animal patient.

Typically, a substantially solid dosage form at ambient temperature of a pharmaceutical formulation according to the first aspect of the present invention is provided in the form of a tablet substantially as hereinbefore described and typically is prepared substantially as hereinbefore described. Alternatively, a substantially solid dosage form of a pharmaceutical formulation according to the first aspect of the present invention may be provided in the form of a rolled preparation, for example, a pill or the like.

It may be generally preferred according to the first aspect of the present invention that the carrier medium, or more particularly the substantially solid dosage form, is converted to a spreading consistency substantially as hereinafter described in greater detail at a temperature that is above ambient temperature but not higher than skin temperature of an animal patient (hereinafter described as the spreading point). In this case, it may also be generally preferred that the above described shaping step of a process according to first aspect of the present invention is carried out at a temperature below the spreading point of either the carrier medium or the substantially solid dosage form.

Typically, it is preferred the carrier medium and more particularly the substantially solid dosage form, of a pharmaceutical formulation according to the first aspect of the present invention may soften, and advantageously may be converted to a spreading consistency, at a temperature in the range of 30 to 37° C. In this way, substantially as hereinbefore described the formulation can soften on application thereof to an area of skin of an animal patient, whereby following application the substantially solid dosage form of the formulation is softened to a consistency that can be substantially completely absorbed by the area of skin so as to effect substantially complete administration of the unit dose of the therapeutic agent to the animal patient.

It is particularly preferred that a pharmaceutical formulation according to the above described first aspect of the present invention has a substantially solid dosage form at ambient temperature that can be softened to a consistency that can be substantially (preferably substantially completely) absorbed by the area of skin of the animal patient, so as to effect substantial administration (preferably substantially complete) of the unit dose of the at least one therapeutic agent to the animal patient, within a time period of less than about 10 minutes, preferably less than about 5 minutes, more preferably less than about 3 minutes and most preferably less than about 1 minute following application to the area of skin,.

More particularly, it is preferred that the shape and configuration of the substantially solid dosage form is determined by the softening point thereof substantially as herein described. It may be preferred that a substantially solid dosage form employed in a pharmaceutical formulation according to the present invention comprises a substantially unitary dosage form; alternatively, a substantially solid dosage form employed in a pharmaceutical formulation according to the present invention can comprise a plurality of substantially discrete substantially solid particles (such as a plurality of granules or the like) that can be absorbed by the skin of an animal patient substantially as hereinbefore described. In the case where the substantially solid dosage form employed in a pharmaceutical formulation according to the present invention can comprise a plurality of substantially discrete particles as herein described, it may be appropriate that such discrete particles be provided in a sealed member (such as a capsule, sachet, blister package or the like) from which the particles can be dispensed and applied to the skin of a patient substantially as herein described.

It may also be preferred that the carrier medium of the substantially solid dosage form of a pharmaceutical formulation according to the above described first aspect of the present invention is further characterised by being suitable, at a temperature of up to about ambient temperature for shaping for incorporation into the substantially solid dosage form of the pharmaceutical formulation. In certain aspects of the present invention, it may be preferred that the carrier medium of the substantially solid dosage form of a pharmaceutical formulation according to the above described first aspect of the present invention is further characterised by being suitable, at a temperature of less than 10° C., preferably less than 0° C., for shaping for incorporation into the substantially solid dosage form of the pharmaceutical formulation. More particularly, it may be preferred that the carrier medium of the substantially solid dosage form is further characterised by being suitable, at a temperature of less than 10° C., preferably less than 0° C., for tableting using techniques substantially as herein described.

Preferably, the carrier medium constitutes not less than about 60%, more preferably not less than about 80% and even more preferably not less than about 90%, by weight based on the weight of a pharmaceutical formulation according to the first aspect of the present invention.

Any base components commonly used for suppositories can be used as a base component of the formulations of the present invention, including those derived from animal, vegetable or mineral origins, and materials partially or totally synthesized. Specific examples given of such base components include oils and fats of animals or vegetable origin, e.g., olive oil, corn oil, castor oil, cottonseed oil, wheat germ oil, cacao butter, hydrogenated oils, etc.; hydrocarbons, e.g., squalane, petrolatum, solid paraffin, liquid paraffin, etc.; and waxes, e.g., jojoba oil, carnauba wax, bees wax, lanolin, etc. As partially or totally synthesized fatty acid esters glycerol, mono-, di-, or triglycerides of medium or higher fatty acid, such as saturated linear fatty acid, e.g., lauric acid, myristic acid, palmitic acid, stearic acid, etc., or unsaturated linear fatty acid, e.g., oleic acid, linoleic acid, linolenic acid, etc, are given. Commercial products of these base components include Witepsol (manufactured by Dynamit Nobel), Pharmasol (manufactured by Nippon Oil and Fats Co.), Isocacao (manufactured by Kao Corp.), SB (manufactured by Taiyo Oil and Fats Co.), Novata (manufactured by Henkel), Suppocire (manufactured by Gattefosse Co.), and the like. Polyethylene glycol, e.g., macrogole, setomacrogole, etc., as well as derivatives thereof, e.g., setomacrogol, are given as examples of other synthetic products.

In order to obtain the desired softening point of the formulations of the present invention, a base can, if necessary, be combined with another base in order to increase or decrease the softening point to obtain a suitable product. For example, in order to decrease the softening point, a base suitable as a plasticizer can be added, e.g., glyceryl monostearate, myristyl alcohol, polysorbate 80, propylene glycol or a combination thereof. In order to increase the softening point, a base which is suitable as a hardener can be added, e.g., beeswax, cetyl alcohol, stearic acid, stearyl alcohol, aluminum monostearate, aluminum distearate, aluminum tristearate, bentonite, magnesium stearate, colloidal silicon dioxide and combinations thereof.

A carrier medium for use according to the above described first aspect of the present invention may comprise any ingredient suitable for use in a pharmaceutical formulation substantially as hereinbefore described, such as any ingredient suitable for use in a tablet formulation substantially as hereinbefore described and possessing the desired properties for achieving dermal administration of a unit dose of at least one therapeutic agent suitable for dermal administration. For example the carrier medium may include a cellulose or may be one or more ingredients selected from the group consisting of ingredients of the type suitable for use in suppositories (including, for example, one or more glycerides (such as, for example, one or more glycerol esters of saturated fatty acids or one or more polyglycolysed glycerides, cocoa butter, theobroma or the like), one or more high molecular weight polyethylene glycol, one or more polyoxyethylene, lanolin and derivatives thereof, and one or more fatty acids, fatty alcohols, fatty acid esters (including, for example, caprylic acid, caprylic triglyceride or the like), any of which preceding ingredients can be optionally mixed with one or more organic oils (including, for example hydrogenated vegetable oils) or the like.

It is often preferred that a carrier medium employed in a pharmaceutical formulation according to the above described first aspect of the present invention comprises, and more preferably consists essentially of, one or more glycerides, including in particular one or more glycerol esters of $C_8$-$C_{18}$ fatty acids or one or more polyglycolysed glycerides.

Suitably, the carrier medium of a pharmaceutical formulation according to the above described first aspect of the present invention comprises, or consists essentially of, a mixture of glycerides, where the glycerides can be one or more mono-glycerides, di-glycerides or tri-glycerides. Suitably the glyceride mixture can comprise glycerides selected from the group consisting of mono-glycerides, di-glycerides and tri-glycerides, where the glycerides comprise glycerol esters of $C_{12}$-$C_{18}$ fatty acids, which glyceride mixture is suitably a Witepsol grade product. More particularly, the carrier medium comprises, or consists essentially of, a Witepsol grade product available under any of the trade marks Witepsol H5, Witepsol H15, Witepsol H32, Witepsol S51, Witepsol S55, Witepsol S58, Witepsol W25 and Witepsol W32. Particularly preferred Witepsol grade products for use as carrier media in pharmaceutical formulations according to the present invention are available under any of the trade marks Witepsol H5, Witepsol H15, Witepsol S51 and Witepsol S55, particularly the Witepsol grade product available under the trade mark Witepsol H15.

It is often preferred that a carrier medium employed in a pharmaceutical product according to the above described first aspect of the present invention consists essentially of a Witepsol grade product substantially as described above.

Alternatively, the carrier medium of a pharmaceutical formulation according to the above described first aspect of the present invention comprises, or consists essentially of, a mixture of glycerides, where the glycerides can be selected from the group consisting of mono-glycerides, di-glycerides and tri-glycerides, the glycerides comprising glycerol esters of $C_8$-$C_{18}$ fatty acids or one or more polyglycolysed glycerides. Suitably such glyceride mixtures are available under the trade marks Gelucire or Suppocire and may typically be any of the following Gelucire 33/01, Gelucire 39/01, Gelucire 43/01, Gelucire 44/14, or any of the Suppocire Standard type, Suppocire N type or Suppocire P type products.

Alternatively a carrier medium suitable for use in a pharmaceutical formulation according to the above described first aspect of the present invention comprises, or consists essentially of, cocoa butter.

Active agents which can be used with the present invention include all drugs which can be delivered onto or through the skin for either a local or systemic effect. These compounds include agents in all of the major therapeutic areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinsonts agents, antiplatelet agents, antiprogestins, antithyroid agents, antitussives, antiviral agents, atypical antidepressants, azaspirodecanediones, barbituates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosupressive agents, laxatives, methylxanthines, monoamine oxidase inhibitors, neuromuscular blocking agents, organic nitrates, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like.

Representative drugs include, by way of example and not for purposes of limitation, bepridil, diltiazem, felodipine, isradipine, nicardipine, nifedipine, nimodipine, nitredipine, verapamil, dobutamine, isoproterenol, carterolol, labetalol, levobunolol, nadolol, penbutolol, pindolol, propranolol, sotalol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone, dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6.alpha.-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, lidocaine, mepivacaine, pramoxine, prilocaine, procaine, proparacaine, tetracaine, alfentanil, choroform, clonidine, cyclopropane, desflurane, diethyl ether, droperidol, enflurane, etomidate, halothane, isoflurane, ketamine hydrochloride, meperidine, methohexital, methoxyflurane, morphine, propofol, sevoflurane, thiamylal, thiopental, acetaminophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, meselamine, methyl salicylate, nabumetone, naproxen, oxyphenbutazone, phenacetin, phenylbutazone, piroxicam, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, disopyramide, encainide, flecainide, indecainide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, pentazocine, isosorbide dinitrate, nitroglycerin, theophylline, phenylephrine, ephidrine, pilocarpine, furosemide, tetracycline, chlorpheniramine, ketorolac, bromocriptine, guanabenz, prazosin, doxazosin, and flufenamic acid.

Other representative drugs include benzodiazepines, such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam, and the like; an antimuscarinic agent such as anisotropine, atropine, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17. beta.-estradiol (or estradiol), semi-synthetic estrogen derivatives such as the esters of natural estrogen, such as estradiol-17. beta.-enanthate, estradiol-17. beta.-valerate, estradiol-3-benzoate, estradiol-17. beta.-undecenoate, estradiol 16,17-hemisuccinate or estradiol-17. beta.-cypionate, and the 17-alkylated estrogens, such as ethinyl estradiol, ethinyl estradiol-3-isopropylsulphonate, and the like; an androgen such as danazol, fluoxymesterone, methandrostenolone, methyltestosterone, nandrolone decanoate, nandrolone phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, and the like.

In embodiments where the-active drugs produce a local effect, the agents include, but are not limited to (in addition to local agents listed above), antiviral agents (e.g., acyclovir and idoxuridine, etc.), antifungal agents (e.g., amphotericin B, clotrimazole, nystatin, ketoconazole, miconazole, butocouazole, haloprogin, etc.), antibiotic agents (penicillins, cephalosporins erythromycin, tetracycline, clindamycin, aminoglycosides, chloramphenicol, polymixin b, bacitracin, neomycin, gentamycin etc.), antiseptics (e.g., povidone-iodine, S methylbenzethonium chloride, etc.), antiparasitics (e.g., lindane, anthralin, etc.) analgesic agents (e.g., methylsalicylate, salicylic acid, dyclonine, aloe vera etc.), local anesthetics (e.g., benzocaine, lidocaine, xylocaine, butamben picrate, etc.), anti-inflammatory agents (e.g., steroidal compounds such as dexamethasone, betamethasone, prednisone, prednisolone, triamcinolone, hydrocortisone, alclometasone, amcinonide, diflorasone, etc. as well as non-steroidal anti-inflammatories ), anti-itch and irritation-reducing compounds (e.g., antihistamines such as diphenhydramine and psoriasis treatments); burn relief compounds (e.g., o-amino-p-toluenesulfonamide, monoacetate, etc.); depigmenting agents (e.g., monobenzone); and hormonal agents (e.g., oestriol).

The compounds that can be used in the present invention, including the compounds listed above, are meant to include all pharmaceuticlly acceptable salts and conjugates.

Other topically-active compounds are listed in Remington's Pharmaceutical Sciences, 17th Ed., Merck Publishing Co., Easton, Pa. (1985), pages 773-791 and pages 1054-1058 (hereinafter Remington's), incorporated herein by reference.

The formulations of the present invention can also be used for other applications, such as for cosmetic purposes, e.g., antiperspirants, sunblocks, keratolitics, skin softeners, fragrances and anti-acne preparations.

These agents include sun screens such as p-dimethylaminobenzoic acid; skin softeners such as urea; keratolytic agents such as salicylic acid; acne agents such as benzoyl peroxide, perfumes and the like.

Suitable antiperspirant compositions include astringent salts. The astringent salts include organic and inorganic salts of aluminum, zirconium, zinc, and mixtures thereof. The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides. Exemplary zirconium compounds include zirconium oxy salts and zirconium hydroxy salts, also referred to as zirconyl salts and zirconyl hydroxy salts Exemplary antiperspirant compounds therefore include, but are not limited to, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof. Numerous other useful antiperspirant compounds are listed in WO 91/19222 and in the Cosmetic and Toiletry Fragrance Handbook, The Cosmetic, Toiletry and Fragrance Association, Inc., Washington, D.C., p. 56, 1989, hereinafter the CTFA Handbook, incorporated herein by reference.

A pharmaceutical formulation according to the above described first aspect of the present invention is suitable for use with any therapeutic agent suitable to be administered dermally substantially as hereinafter described in greater detail. A pharmaceutical formulation according to the above described first aspect of the present invention is, however, particularly suitable for dermally administering at least one local anaesthetic to an animal patient and it may be preferred, therefore, that a pharmaceutical formulation according to the above described first aspect of the present invention comprises at least one local anaesthetic (in particular lignocaine, also known as lidocaine) as a therapeutic agent to be administered thereby. Alternatively, a pharmaceutical formulation according to the above described first aspect of the present invention can be particularly suitable for dermally administering at least one corticosteroid to an animal patient and it may be preferred, therefore, that a pharmaceutical formulation according to the above described first aspect of the present invention comprises at least one corticosteroid (in particular hydrocortisone) as a therapeutic agent to be administered thereby.

A particularly preferred pharmaceutical formulation according to the above described first aspect of the present invention comprises, therefore, a formulation for effecting dermal administration of lignocaine to an animal patient, which formulation at ambient temperature has a substantially solid dosage form comprising a unit dose of lignocaine in admixture with a carrier medium comprising Witepsol S55, the formulation being characterised by the substantially solid dosage form being softenable on application thereof to an area of skin of an animal patient, whereby following application to the area of skin the substantially solid dosage form is softened to a consistency that can be absorbed (substantially completely) by the area of skin so as to effect substantial administration (substantially complete) of the unit dose of lignocaine -to the animal patient.

An alternative particularly preferred pharmaceutical formulation according to the above described first aspect of the present invention comprises a formulation for effecting dermal administration of hydrocortisone to an animal patient, which formulation at ambient temperature has a substantially solid dosage form comprising a unit dose of hydrocortisone in admixture with a carrier medium consisting essentially of cocoa butter, the formulation being characterised by the substantially solid dosage form being softenable on application thereof to an area of skin of an animal patient, whereby following application to the area of skin the substantially solid dosage form is softened to a consistency that can be absorbed (substantially completely) by the area of skin so as to effect substantial administration (substantially complete) of the unit dose of hydrocortisone to the animal patient.

A still further alternative particularly preferred pharmaceutical formulation according to the above described first aspect of the present invention comprises a formulation for effecting dermal administration of hydrocortisone to an animal patient, which formulation at ambient temperature has a substantially solid dosage form comprising a unit dose of hydrocortisone in admixture with a carrier medium consisting essentially of Witepsol H15, the formulation being characterised by the substantially solid dosage form being softenable on application thereof to an area of skin of an animal patient, whereby following application to the area of skin the substantially solid dosage form is converted to a consistency that can be absorbed (substantially completely) by the area of skin so as to effect substantial administration (substantially complete) of the unit dose of hydrocortisone to the animal patient.

According to the above described first aspect of the present invention, there is still further provided a pharmaceutical product comprising a pharmaceutical formulation according to the first aspect of the present invention substantially as hereinbefore described together with a covering member that can be arranged to substantially cover the pharmaceutical formulation when the latter is applied to an area of skin of the animal patient and means for adhering the covering member to an area of skin of the animal patient.

Preferably a product according to the above described first aspect of the present invention is provided in the form of a medicinal transdermal patch comprising a pharmaceutical formulation according to the first aspect of the present invention substantially as hereinbefore described together with a substantially flexible substrate suitable for substantially overlying the pharmaceutical formulation when the latter is applied to an area of skin of an animal patient, the substrate having adhesive means for adhering the substrate to an area of skin of an animal patient (typically in the form of an adhesive coating applied thereto). The patch can be adhered to the skin of an animal patient, thereby holding the substantially solid dosage form of the pharmaceutical formulation in contact with the skin so that the temperature of the substantially solid dosage form is raised above its softening point to a consistency that can be absorbed by the skin so as to achieve administration of the unit dose of the therapeutic agent to the animal patient.

Suitably a substrate of a patch as provided by the above described first aspect of the present invention is substantially impermeable to the pharmaceutical formulation. Suitably, the substrate may be a polymer film of the type suitable for use in conventional plasters.

In an alternative embodiment of a product according to the above described first aspect of the present invention the product may require the covering member to be in the form of a plastic film, which although arranged in use to overlie a pharmaceutical formulation when the latter has been applied to the skin of a patient, is spaced from the applied formulation thereby creating a humid local atmosphere adjacent the area of skin to which the formulation has been applied. In this way, the humid local atmosphere can aid softening of the substantially solid dosage form for absorption by the skin of the patient.

It will be understood that where the therapeutic agent is for treatment of a local condition of the skin substantially as hereinafter described in greater detail, substantial absorption by at least the outer epidermal layers of the skin of the animal patient will suffice for treatment of the patient and substantial transdermal passage into the bloodstream is not required and indeed in some instances will not be desirable.

It may be advantageous to employ in a pharmaceutical formulation according to the first aspect of the present invention substantially as hereinbefore described, and consequently in a process according to the present invention of preparing the same, one or more tableting aids, which may, for example, be selected from antiadhesives (for example, talc or the like); flow aids (for example, silicon dioxide or the like); and compaction aids (for example, microcrystalline cellulose, dicalcium phosphate or the like) or any other ingredient suitable for use as a tableting aid in formulations and processes according to the above described first aspect of the present invention.

The present invention is also concerned with the provision of a pharmaceutical formulation containing a unit dose of at least one therapeutic agent substantially as hereinafter described in greater detail and having, at ambient temperature prior to application to an area of skin of an animal patient, a spreading consistency suitable for application to the area of skin of the animal patient, whereby following application the formulation can be absorbed so as to effect administration of the unit dose of the therapeutic agent.

The present invention is, therefore, also concerned with the provision of an ointment or cream for dermal administration to an animal patient and containing a unit dose of at least one therapeutic agent substantially as hereinafter described in greater detail.

According to a second aspect of the present invention, therefore, there is provided a process of preparing a pharmaceutical formulation having, at ambient temperature prior to application to an area of skin of an animal patient, a spreading consistency suitable for application to the area of skin of the animal patient (in other words typically a pharmaceutical formulation in the form of an ointment or cream at ambient temperature), which process comprises preparing a mixture of at least one therapeutic agent and a carrier medium therefor, followed by shaping, substantially as hereinbefore described with reference to a process according to a first aspect of the present invention and allowing the mixture to attain a temperature at which the mixture has a spreading consistency (this temperature is herein referred to as a spreading point of a pharmaceutical formulation according to the present invention and is hereinafter described in greater detail).

Typically in a process according to the above described second aspect of the present invention, during shaping of at least a portion of a mixture substantially as hereinbefore described, a substantially solid form is prepared which is subsequently converted to a spreading consistency at a temperature below ambient temperature and typically at a temperature not higher than about 15° C., advantageously at a temperature of not higher than about 10° C., for example, not higher than about 0° C.

It is generally preferred that in a process according to the above described second aspect of the present invention a substantially solid form is prepared by-shaping at a temperature lower than the spreading point of the pharmaceutical formulation and typically not higher than about 15° C., advantageously at a temperature of not higher than about 10° C., for example, not higher than about 0° C.

According to a particular embodiment of the second aspect of the present invention, there is provided a process of preparing a pharmaceutical formulation containing a unit dose of at least one therapeutic agent suitable for dermal administration to an animal patient and having, at ambient temperature prior to application to an area of skin of an animal patient, a spreading consistency suitable for application to the area of skin of the animal patient, the process comprising:

(a) admixing the at least one therapeutic agent with at least one carrier medium therefor so as to obtain a mixture thereof; and (b) at a temperature of not higher than about 15° C., shaping at least a portion of the mixture obtained by step (a).

Advantageously, the shaping step is carried out at a temperature of not higher than about 10° C., for example, not higher than about 0° C. substantially as hereinbefore described. Advantageously a shaped portion as obtained by step (b) is packaged substantially as hereinafter described in greater detail, for example in hermetically sealed individual receptacles therefor and suitably the packaged portion can subsequently be allowed to warm to ambient temperature.

Preferably, therefore, a process according to the second aspect of the present invention can also include the step of packaging a substantially solid form prepared substantially as hereinbefore described prior to the substantially solid form being allowed to warm to its spreading point (in other words prior to the substantially solid form attaining a temperature at which the substantially solid form is converted to a spreading consistency). In this way a packaged dosage, and more particularly a plurality of substantially discrete packaged dosages of a pharmaceutical formulation substantially as hereinafter described in greater detail, according to the second aspect of the present invention can be provided. Such a packaged dosage, or discrete packaged dosages, of a pharmaceutical formulation according to the second aspect of the present invention in the form of a cream or ointment can be easily handled and applied by a human patient or attendant physician, whilst also permitting relatively accurate dosing of the one or more therapeutic agents to be administered thereby.

A particularly preferred process according to the second aspect of the present invention comprises, in the order specified:

(a) admixing at least one therapeutic agent suitable for dermal administration to an animal patient and a carrier medium therefor so as to obtain a mixture thereof;

(b) cooling (preferably at a temperature of not higher than about 10° C., preferably not higher than about 0° C.) the mixture obtained by step (a) so as to effect substantial solidification thereof;

(c) shaping at least a portion of the substantially solidified mixture obtained by step (b) to provide a substantially solid form (typically at a temperature of not higher than about 15° C., advantageously at a temperature of not higher than about 10° C., for example, not higher than about 0° C.); and (d) allowing the resulting substantially solid form obtained by step (c) to reach ambient temperature so as to be converted to a spreading consistency.

Substantially as herein described it may be preferred that a pharmaceutical formulation as provided by the present invention is substantially free of preservatives substantially as hereinafter described in greater detail and in such cases it is preferred that a process according to the present invention is carried out under aseptic conditions.

Also substantially as herein described it may be preferred that a pharmaceutical formulation provided by the present invention is substantially free of antioxidants substantially as hereinafter described in greater detail and in such cases it is preferred that, where a process according to the present invention includes packaging of the pharmaceutical formulation, such packaging is carried out in a substantially inert atmosphere, such as nitrogen or the like.

According to the second aspect of the present invention there is also provided a pharmaceutical formulation containing a unit dose of at least one therapeutic agent suitable for dermal administration to an animal patient and having, at ambient temperature prior to application to an area of skin of an animal patient, a spreading consistency suitable for application to the area of skin of the animal patient.

More particularly, there is also provided an ointment or cream comprising a unit dose of at least one therapeutic agent suitable for dermal administration to an animal patient and a major proportion of a carrier medium therefor, the ointment or cream having a spreading point lower than ambient temperature.

There is also provided a pharmaceutical product comprising a plurality of discrete dosages of a pharmaceutical formulation according to the second aspect of the present invention, each dosage having a spreading consistency at a temperature of lower than skin temperature of an animal patient and more particularly each dosage having a spreading consistency typically at ambient temperature, more typically a temperature of not higher than about 15° C., for example not higher than about 10° C.

According to a particularly preferred embodiment of the second aspect of the present invention there is provided a pharmaceutical product for effecting dermal administration of at least one therapeutic agent suitable for dermal administration to an animal patient, the product comprising a plurality of discrete dosages each containing the at least one therapeutic agent, each dosage form comprising an admixture comprising:

a unit dose of the at least one therapeutic agent; and a carrier medium having at ambient temperature prior to application to an area of skin of the animal patient a spreading consistency suitable for application to the area of skin;

whereby following application to the area of skin of the animal patient the dosage can be substantially absorbed (substantially completely) by the area of skin of the animal patient so as to effect substantial-(substantially complete) administration of the unit dose of the therapeutic agent to the animal patient.

Preferably, a carrier medium as employed in a pharmaceutical formulation according to the second aspect of present invention, and more particularly a pharmaceutical formulation according to the second aspect of the present invention, may have a spreading point of not higher than about 15° C.

Advantageously, a carrier medium as employed in a pharmaceutical formulation according to the second aspect of present invention, and more particularly a pharmaceutical formulation according to the second aspect of the present invention, may have a spreading point of not higher than about 10° C., for example, not higher than about 0° C. Such pharmaceutical formulations according to the second aspect of the present invention may, therefore, have spreading points below ambient temperature. It will be appreciated that, where the spreading point is below ambient temperature, the formulation will not be solid when stored or applied at ambient temperature. Such formulations will in general be manufactured as substantially solid preparations at a temperature beneath the spreading point substantially as hereinbefore described, but may then be allowed to warm to a temperature exceeding the spreading point after packaging again substantially as hereinbefore described.

Preferably, the carrier medium constitutes not less than about 60%, more preferably not less than about 80% and even more preferably not less than about 90%, by weight based on the weight of a pharmaceutical formulation according to the second aspect of the present invention.

The carrier medium for use in a pharmaceutical formulation according to the second aspect of the present invention may be any suitable material that is acceptable for dermal use substantially as hereinbefore described. In the case of a pharmaceutical formulation which at skin temperature is to be in the form of a cream, the carrier medium may comprise an emulsion. In the case of a pharmaceutical formulation which at skin temperature is to be in the form of an ointment, the carrier medium may comprise an oil.

A carrier medium suitable for use in a pharmaceutical formulation according to the present invention may be selected from the group consisting of ingredients of the type suitable for use in suppositories (including, for example, one or more glycerides, such as, for example, one or more glycerol esters of saturated fatty acids or one or more polyglycolysed glycerides, cocoa butter, theobroma or the like), one or more high molecular weight polyethylene glycol, one or more polyoxyethylene, lanolin and derivatives thereof, one or more fatty acids, fatty alcohols, fatty esters (including, for example, caprylic acid, caprylic triglyceride or the like), and one or more organic oil (including, for example, hydrogenated vegetable oils) or the like.

A particularly suitable carrier medium for use in a pharmaceutical formulation according to the second aspect of the present invention consists essentially of an intimate mixture of cocoa butter and at least one organic oil, such as castor oil or almond oil.

There is still further provided by the present invention a method of treating an animal patient by dermally administering to the animal patient a pharmaceutical formulation substantially as hereinbefore described so as to administer to the animal patient a unit dose of at least one therapeutic agent suitable for dermal administration to the animal patient as herein described.

More particularly, there is provided by the present invention a method of dermally administering at least one therapeutic agent to an animal patient, which therapeutic agent is provided by a pharmaceutical formulation according to the first aspect of the present invention substantially as hereinbefore described and which method of administration comprises:

applying to an area of skin of an animal patient a substantially solid dosage form of a pharmaceutical formulation according to the first aspect of the present invention substantially as hereinbefore described;

maintaining the applied pharmaceutical formulation in contact with the area of skin of the animal patient so as to effect softening of the substantially solid dosage form to a consistency that can be absorbed (substantially completely) by the area of skin of the animal patient; and thereby administering to the animal patient the unit dose (substantially completely) of the therapeutic agent.

There is also provided by the present invention a method of dermally administering at least one therapeutic agent to an animal patient, which therapeutic agent is provided by a pharmaceutical formulation according to a second aspect of the present invention substantially as hereinbefore described, which method comprises:

applying to an area of skin of an animal patient a pharmaceutical formulation according to the second aspect of the present invention substantially as hereinbefore described (typically by dispensing from a pharmaceutical product according to the second aspect of the present invention substantially as hereinbefore described at least one discrete dosage containing a unit dose of at least one therapeutic agent suitable for dermal administration to an animal patient);

rubbing the applied pharmaceutical formulation according to the second aspect of the present invention substantially as hereinbefore described (or the at least one dispensed discrete dosage) substantially into the area of skin of the animal patient, whereby the applied pharmaceutical formulation according to the second aspect of the present invention substantially as hereinbefore described (or the at least one dispensed discrete dosage) can be absorbed (substantially completely) by the skin; and thereby administering (substantially completely) to the animal patient the unit dose of the therapeutic agent.

There is still further provided by the present invention, for use in the manufacture of a medicament for dermal administration to an animal patient, a pharmaceutical formulation substantially as hereinbefore described and still further there is provided a pharmaceutical formulation or product substantially as herein described in any one of the Examples.

The term "therapeutic agent" as used herein denotes any active substance suitable to be dermally administered to an animal patient (particularly human) and being suitable for use in any formulation or product of the present invention (whether according to the above described first or second aspect of the present invention) and may typically comprise any active substance that can as such be administered dermally as described above so as to have a desired pharmacological therapeutic effect on an animal (particularly human) body. The term "therapeutic agent" as used herein also includes any pharmaceutically acceptable equivalent thereof, such as a pharmaceutically acceptable salt, ester, prodrug or metabolite thereof. Isomers of all disclosed agents are also encompassed by this disclosure.

The terms "dermally administered" or "dermal administration" as used herein include (i) administration of a therapeutic agent suitable for use in the present invention for local or topical treatment of a disorder of the skin substantially as hereinafter described in greater detail and (ii) administration of a therapeutic agent suitable for use in the present invention for non-local treatment, in other words for administration into the blood stream of an animal (particularly human) patient for systemic treatment substantially as hereinafter described in greater detail.

The term "treatment" as used herein denotes the treatment of established conditions as well as the prophylaxis thereof. The precise treatment conditions for any pharmaceutical formulation, product or method according to the present invention will of course depend on the precise nature of a condition being treated, the age and sex of an animal (particularly human) patient and will ultimately be at the discretion of an attendant physician.

As described above therapeutic agents for use according to the present invention may have local (often this is preferred) activity or non-local activity.

Therapeutic agents having local activity for use according to any aspect of the present invention include, for example, active substances for use in the treatment of disorders of the skin, such disorders including, by way of example, psoriasis, eczema, acne, nappy rash and other inflammatory disorders of the skin; bacterial or fungal infections of the skin; malignant diseases of the skin; warts and the like.

Advantageously, therapeutic agents having local activity for use. according to the present invention can be selected from the group consisting of local anaesthetics, corticosteroids, antibacterial agents, antifungal agents or any therapeutically effective combination thereof.

More particularly, therapeutic agents having local activity for use according to the present invention can be selected from the group consisting of tetracaine, benzocaine, lignocaine, hydrocortisone, beclomethazone diproprionate, clobetasol proprionate, fluticasone proprionate, ichthammol, lithium succinate, coal tar, dithranol, benzoyl peroxide, tretinoin, sulphur, vitamin D and derivatives thereof, framycetin, chlortetracycline hydrochloride, fusidic acid, clotrimazole, econazole, amorolfine and terbenafine, or any therapeutically effective combination thereof.

The present invention is particularly suitable for achieving local delivery of lignocaine or hydrocortisone substantially as hereinafter described in greater detail.

Therapeutic agents having non-local activity for use according to any aspect of the present invention include, for example, active substances for use in the treatment or prevention of various systemic disorders and their symptoms, such as disorders of the cardiovascular system, disorders of the muscles or joints, disorders of the organs. More particularly, therapeutic agents having non-local activity for use according to any aspect of the present invention include, for example, active substances for use as vasodilators, active substances for the treatment of motion sickness, contraceptive agents, hormone replacement agents, painkillers, and smoking cessation aids, or any therapeutically effective combination thereof.

Advantageously, therapeutic agents having non-local activity for use according to any aspect of the present invention are selected from the group consisting of nitroglycerin, scopolamine, estradiol, norethisterone, fentanyl and nicotine, or any therapeutically effective combination thereof.

Therapeutic agents employed in the present invention should be present in a therapeutically effective concentration, for example, at least 0.01% by weight based on the total weight of the pharmaceutical formulation. In general, the therapeutic agent will be present in an amount of not more than 10%, advantageously, not more than 2%, more advantageously not more than 5%, preferably not more than 1%, more preferably not more than 0.05%, by weight based on the total weight of the pharmaceutical formulation.

Pharmaceutical formulations according to the present invention may suitably further comprise, where appropriate, additional ingredients such as one or more hardeners, one or more plasticisers or the like. Suitable hardeners include, for example, beeswax, cetyl alcohol, stearic acid, stearyl alcohol, aluminum monostearate, bentonite or the like. Suitable plasticisers include, for example, glyceryl monostearate, myristyl alcohol, polysorbate 80, propylene glycol or the like.

Pharmaceutical formulations according to the present invention may suitably further comprise, where appropriate, additional ingredients such as one or more penetration enhancers (which may be surfactants, alcohols, esters, glycols or the like or any other suitable penetration enhancer), humectants, surfactants (which may be cationic, non-ionic, anionic or polymeric), emulsifiers, antioxidants, preservatives, clays, anti-foaming agents, spreading agents, emollients, barriers, solubilising agents for the therapeutic agent and the like.

In a particular aspect of the present invention, however, it is generally preferred that pharmaceutical formulations according to the present invention are substantially free of preservatives of the type generally included in formulations intended for dermal administration, or at least may include such preservatives in amounts less than generally required in formulations intended for dermal administration, or at least may include such preservatives in amounts that generally do not provoke substantial allergic reactions in susceptible patients substantially as hereinafter described. Such preservatives generally employed in formulations intended for dermal administration are present to obviate contamination of such dermal formulations due to repeated handling of such formulations and may not be required by the present invention due to the unit dosing onto the skin that can be achieved by the present invention. Indeed the use of such preservatives to obviate against contamination due to repeated handling can, in some patients, be detrimental in provoking allergic reactions in susceptible patients and the present invention may be advantageous in obviating such allergic reactions in susceptible patients. Preservatives that have been associated with allergic reactions include chlorocresol, hydroxybenzoates (parabens), polysorbates, sorbic acid and the like, and are known to be present in a large number of prior art topical formulations, including for example formulations available under any of the following trade marks—Drapolene, Medicaid, Siopel, Sprilon, Eurax, Efcortelan, Mildison, Fucidin H, Nystafrom Quinocort, Terra-Cortril Nystatin, Timodine, Locoid, Locoid Crelo, Modrasone, Propaderm, Betnovate, Betnovate RD, Diprosone, Dermovate, Eumovate, Trimovate, Nerisone, Haelan, Synalar, Ultralanum Plain, Zorac, Carbo-Dome, Exorex, Differin, Exelderm and the like.

Pharmaceutical formulations according to the present invention may, however, further comprise one or more preservatives, such as phenoxyethanol or the like, that are included typically to substantially obviate contamination of the formulations according to the present invention during manufacture but are not generally of the type employed to obviate infection due to manual application as hereinbefore described.

It may also be preferred that pharmaceutical formulations according to the present invention may be substantially free of antioxidants of the type generally included in formulations for dermal administration, or at least may include such antioxidants in amounts less than generally required in formulations intended for dermal administration, or at least may include such antioxidants in amounts that generally do not provoke substantial allergic reactions in susceptible patients substantially as hereinafter described. Such antioxidants generally employed in formulations intended for dermal administration are generally present to prevent fats present in such formulations becoming rancid, may be useful in general storage and are primarily present to prevent in use oxidation following opening. Such antioxidants may not be required by the present invention, or at least required to a lesser extent than employed in prior art formulations, or more particularly may be employed at concentrations that do not generally provoke substantial allergic reactions in susceptible patients, due to the unit dosing onto the skin that can be achieved by the present invention. The use of such antioxidants can, in some patients, be detrimental in provoking allergic reactions in susceptible patients and the present invention may be advantageous in obviating such allergic reactions in susceptible patients. Antioxidants that have been associated with allergic reactions include butylated hydroxyanisole, butylated hydroxytoluene and the like, and are known to be available in prior art topical formulations, such as those formulations available under any of the trade marks Imuderm, Siopel and the like.

The term "softening point" as used herein refers to a temperature at which a substantially solid dosage form as employed in a pharmaceutical formulation according to the first aspect of the present invention as hereinbefore described starts to soften to a consistency that can be absorbed by the skin of a patient so as to administer a unit dose of a therapeutic agent present in the formulation to the patient.

The "softening point" of a substantially solid dosage form of a pharmaceutical formulation according to the first aspect of the present invention substantially as hereinbefore described can be determined visibly as the temperature at which the substantially solid dosage form starts to soften to a consistency that can be absorbed by the skin of a patient and as such can advantageously be substantially completely absorbed by the skin of the patient so as to leave substantially no undesirable residue on the skin of a patient.

Alternatively, the "softening point" of a substantially solid dosage form of a pharmaceutical formulation according to the first aspect of the present invention substantially as hereinbefore described can be determined using a TA-XT2 texture analyser, suitably equipped with a 5 kg load cell. The equipment is enclosed in a temperature controlled chamber (capable of operating in the region of −60° C. to 200° C.). A tablet or other substantially solid dosage form according to the present invention may be enclosed in the chamber at the specified temperature for a time of at least 10 minutes. A 3 mm flat faced probe is pushed into the tablet or other substantially solid dosage form according to the present invention for a distance of 1 mm at a speed of 0.1 mm. $\text{sec}^{-1}$.

Measurements can be repeated at temperature increments of 1° C. and, at the temperature at which the peak force of resistance recorded (as measured by Texture Exceed software) falls to below 50% of that for a "solid" tablet or other substantially solid dosage form according to the present invention, the tablet or other dosage form is deemed to have "softened".

The term "spreading point" as used herein in relation to a pharmaceutical formulation according to either the first or second aspect of the present invention refers to a temperature at which the formulation has a "spreading" consistency, for example, the formulation may flow under its own weight or at least can be spread upon the skin of an animal patient, for example, using finger pressure. That mobility of a formulation having a spreading consistency may promote the absorption of a therapeutic agent into the skin by allowing movement of the therapeutic agent towards the skin, for example, by diffusion. The spreading point of a preparation may be measured using the TA-XT2 texture analyser mentioned above in relation to measurement of softening point and with this analyser the spreading point of a formulation is the temperature at which outward flow of the formulation is first observed on advance of the flat faced probe into the preparation.

The term "unit dose" means a formulation suitable for single administration which contains an effective amount of an agent to be administered, for example, a therapeutically active agent or a cosmetic agent.

The formulations of the present invention can be packaged in a so-called blister pack. Blister packs are well known in the packaging industry and are widely used for the packaging of pharmaceutical unit dosage forms. Blister packs generally consist of a sheet of relatively stiff material covered with a foil of a preferably transparent plastic material. During the packaging process recesses are formed in the plastic foil. The recesses have the size and shape of the formulations to be packed. The formulations of the present invention can be placed in the recesses and the sheet of relatively stiff material is sealed against the plastic foil at the face of the foil which is opposite from the direction in which the recesses were formed. As a result, the formulations are sealed in the recesses between the plastic foil and the sheet. Preferably the strength of the sheet is such that the formulation can be removed from the blister pack by manually applying pressure on the recesses whereby an opening is formed in the sheet at the place of the recess, without affecting the integrity of the formulation. In other embodiments, the foil can be peeled away. The formulations of the present invention can then be removed via said opening.

It may be desirable to provide a memory aid on the blister-pack, e.g., in the form of numbers corresponding with the days of the regimen which the formulations so specified should be applied. Another example of such a memory aid is a calendar printed on the card, e.g., as follows "First Week, Monday, Tuesday, etc., Second Week, Monday, Tuesday," etc. Other variations of memory aids will be readily apparent. A "daily dose" can be a single formulation or several formulations to be applied on a given day.

The formulations of the present invention are preferably in solid form during the final manufacturing step and during packaging, and preferably at the time of administration.

The present invention will now be further illustrated by the following Examples, which do not limit the invention in any way.

EXAMPLE 1

| Tablet Ingredients: | |
|---|---|
| Lignocaine | 2% |
| Tween 62 (Emulsifier) | 5% |
| Witepsol S55* | 93% |

*A low melting (33° C. to 35° C.) triglyceride.
Percentages are by weight based on the total weight of the combined ingredients.

Method of Preparation:
1. The ingredients were mixed for 5 minutes in a high shear mixer blender, to form a granular mixture. The mixture was cooled by immersion in dry ice contained in a receptacle.
2. The tablets were compressed on a Manesty F press using 10 mm flat faced zirconia tooling. The mixture was compacted under the compression and then solidified to form a tablet.

EXAMPLE 2

| Tablet Ingredients: | |
|---|---|
| Hydrocortisone | 0.005 g |
| Cocoa Butter | 0.275 g |

Method of preparation:

Cocoa Butter was gently melted down until molten and homogenous. Hydrocortisone was then added and was mixed in whilst gently heating. The mixture was cooled and then left in the fridge overnight to harden. Once hard the solid was then broken down and granulated.

The tablets were compressed on a TA-XT2 using 10 mm flat faced stainless steel/Zirconia tooling. The mixture was compacted under the compression and then solidified to form a tablet.

EXAMPLE 3

| Tablet Ingredients: | |
| --- | --- |
| Hydrocortisone | 0.005 g |
| Witepsol H15 | 0.334 g |

Method of preparation:

Witepsol H15 was gently melted down until molten and homogenous. Hydrocortisone was then added and was mixed in whilst gently heating. The mixture was cooled and then left in the fridge overnight to harden. Once hard the solid was then broken down and granulated.

The tablets were compressed on a TA-XT2 using 10 mm flat faced stainless steel/Zirconia tooling. The mixture was compacted under the compression and then solidified to form a tablet.

EXAMPLE 4

Dosage Ingredients:
 Hydrocortisone
 Carrier

Four different carrier formulations were used in dosages prepared according to Example 4 as follows.

Formulation 1:
 50% Castor Oil
 50% Cocoa Butter

Formulation 2:
 60% Castor Oil
 40% Cocoa Butter

Formulation 3:
 70% Castor Oil
 30% Cocoa Butter

Formulation 4:
 70% Almond Oil
 30% Cocoa Butter

Method of Preparation:

Cocoa Butter and selected oil as described in formulations 1 to 4 above were gently melted down until molten and homogenous. Hydrocortisone was then added and was mixed in whilst gently heating. The mixture was cooled, then left in the freezer to harden. Once hard the solid was broken down and then granulated at a low temperature.

The dosages were prepared by compressing on a TA-XT2 using 10 mm flat faced stainless steel/Zirconia tooling. The mixture was compacted under the compression at a temperature of 0 to −4° C. and solidified to form solid dosages which were allowed to reach room temperature and subsequently soften.

The invention claimed is:

1. A pharmaceutical formulation for dermal administration to a mammal, the formulation being a solid, unit dosage form and comprising a unit dose of a therapeutically effective amount of at least 1% by weight of one or more therapeutic agents and a pharmaceutically acceptable carrier medium, said formulation being solid at ambient temperature and having a softening point from 30° C. to not higher than 35° C., such that upon being placed in continuous contact with an area of the skin of a mammalian patient to be treated, it is softened or melted to effect administration of the unit dose of said therapeutic agent to the mammalian patient within a time period of less than 5 minutes, wherein said formulation is in the form of a tablet and has at least one surface which is flat, and wherein the carrier medium comprises cocoa butter or one or more glycerides, where the glycerides are selected from the group consisting of mono-glycerides, di-glycerides and tri-glycerides and the formulation is not provided as a medicinal transdermal patch or plaster.

2. A pharmaceutical formulation as claimed in claim 1, comprising a compacted granulate of the dose of a therapeutic agent and a pharmaceutically acceptable carrier medium, said compacted granulate having a softening point of not higher than 35° C.

3. The formulation of claim 2, wherein the compacted granulate is cooled to a temperature of not more than 15° C. prior to compaction.

4. The formulation of claim 2, wherein the compacted granulate is cooled to a temperature of not more than 10° C. prior to compaction.

5. The formulation of claim 2, wherein the compacted granulate is cooled to a temperature of not more than 0° C. prior to compaction.

6. The formulation as claimed in claim 1, which has an aspect ratio (wall:face) of less than 1:1.

7. The formulation of claim 1, wherein said therapeutic agent is a locally active agent and said unit dose is effective to treat an area of the skin of said mammal.

8. The formulation of claim 1, which comprises at least one concave surface.

9. The formulation of claim 1, which comprises at least one convex surface.

10. The formulation of claim 1, which comprises two flat surfaces.

11. The formulation of claim 1, which has a total weight from about 50 mg to less than 1 g.

12. The formulation of claim 11, which has a total weight from 100 mg to 900 mg.

13. A pharmaceutical formulation according to claim 1, wherein the therapeutic agent is selected from the group consisting of ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbituates, benzodiazepines, benzothiadiazides, beta-adrenergic agonists, betaadrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosupressive agents, laxatives, methylxanthines, monoamine oxidase inhibitors, neuromuscular blocking agents, organic nitrates, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and pharmaceutically acceptable salts, and any therapeutically effective combination thereof.

14. A pharmaceutical formulation according to claim 13, comprising an analgesic agent and an anti-inflammatory agent.

15. A pharmaceutical formulation according to claim 14, wherein the anti-inflammatory agent is a non-steroidal anti-inflammatory agent, and the analgesic agent is an opiate or an opiate-based agent.

16. A pharmaceutical formulation according to claim 1, wherein the therapeutic agent is a non-steroidal anti-inflammatory agent.

17. A pharmaceutical formulation according to claim 16, wherein the therapeutic agent is selected from the group consisting of diclofenac, ketolorac, ibuprofen, ketoprofen, naproxen, aspirin and paracetamol, pharmaceutically acceptable salts thereof; and any therapeutically effective combination thereof.

18. The formulation according to claim 1, further comprising a penetration enhancer.

19. The formulation according to claim 18, wherein the penetration enhancer is menthol.

20. The formulation of claim 1, wherein said patient is human.

21. The pharmaceutical formulation of claim 1, wherein said therapeutic agent is selected from the group consisting of antiviral agents, antifungal agents, corticosteroids, antibacterial agents, antibiotic agents, antiseptics, antiparasitics, analgesics, anti-inflammatory agents, local anesthetics, and anti-itch and irritation-reducing compounds, pharmaceutically acceptable salts; and any therapeutically effective combinations thereof.

22. A pharmaceutical formulation according to claim 1, wherein the therapeutic agent is selected from the group consisting of tetracaine, benzocaine, lignocaine, hydrocortisone, beclomethasone diprorionate, clobetasol proprionate, fluticasone proprionate, ichthammol, lithium succinate, coal tar, dithranol, benzoyl peroxide, tretinoin, sulphur, vitamin D and prodrugs thereof, framycetin, chlortetracycline hydrochloride, fusidic acid, clotrimazole, econazole, amorolfine and terbenafine, and any therapeutically effective combination thereof.

23. The pharmaceutical formulation according to claim 1, wherein said locally active agent is selected from the group consisting of bupivacaine, levobupivacaine, ropivacaine, benzocaine, dibucaine, procaine, chloroprocaine, prilocaine, mepivacaine, lignocaine, etidocaine, tetracaine, lidocaine, and xylocaine and mixtures thereof.

24. The pharmaceutical formulation according to claim 1, wherein the therapeutic agent is hydrocortisone.

25. The pharmaceutical formulation of claim 1, wherein the therapeutic agent is a non-steroidal anti-inflammatory agent.

26. A pharmaceutical formulation according to claim 1, wherein the therapeutic agent is diclofenac, ketolorac, ibuprofen, ketoprofen, naproxen, aspirin or paracetamol, pharmaceutically acceptable salts or conjugates thereof or any therapeutically effective combination thereof.

27. The pharmaceutical formulation of claim 1, wherein said therapeutic agent is a steroidal compound selected from the group consisting of dexamethasone, betamethasone, prednisone, prednisolone, triamcinolone, hydrocortisone, alclometasone, amcinonide, diflorasone, pharmaceutically acceptable salts thereof or any therapeutically effective combinations thereof.

28. The pharmaceutical formulation of claim 1, further comprising one or more therapeutic agents having a systemic effect.

29. The pharmaceutical formulation of claim 28, wherein said therapeutic agent is selected from the group consisting of anti-inflammatories, an antihypertensive agent, a cardiovascular agent, a hormonal agent and an analgesic, vasodilators, active substances for the treatment of motion sickness, gastric acidity and peptic ulcers, contraceptive agents, anti-asthmatic agents, anti-epileptic agents, or smoking cessation aids, pharmaceutically acceptable salts thereof; and any therapeutically effective combinations thereof.

30. The pharmaceutical formulation according to claim 29, wherein the therapeutic agent is selected from the group consisting of nitroglycerin, scopolamine, estradiol, norethisterone, fentanyl, morphine, pethidine, oxycodone, oxymorphone, codeine, hydrocodone, hydromorphone, buprenorphine, nicotine, diclofenac, ketolorac, ibuprofen, ketoprofen, naproxen, aspirin and paracetamol, pharmaceutically acceptable salts thereof; and any therapeutically effective combinations thereof.

31. A pharmaceutical formulation according to claim 29, wherein the therapeutic agent is selected from the group consisting of beta-adrenergic agonists, anti-muscarinic agents, steroids, leukotriene antagonists and cromones, pharmaceutically acceptable salts thereof; and any therapeutically effective combinations thereof.

32. A pharmaceutical formulation according to claim 31, wherein the therapeutic agent is selected from the group consisting of salbutamol, salmeterol, formoterol, clenbuterol, ipratropium, glycotropium, tiotropium, oxytropium, beclomethasone, betamethasone, fluticasone, budesonide, montelukast, cromolyn sodium, nedocromil and pharmaceutically acceptable salts thereof; and any therapeutically effective combinations thereof.

33. A pharmaceutical formulation according to claim 29, wherein the therapeutic agent is selected from the group of benzodiazapines.

34. A pharmaceutical formulation according to claim 33, wherein the therapeutic agent is selected from the group consisting of diazepam, lorazepam, clonazepam, clobazam, medazolam, pharmaceutically acceptable salts thereof; and any therapeutically effective combinations thereof.

35. A pharmaceutical formulation according to claim 29, wherein the therapeutic agent is omeprazole or lansoprazole.

36. The pharmaceutical formulation of claim 1, wherein said formulation is a compressed tablet.

37. The pharmaceutical formulation of claim 1, wherein said formulation is free of preservatives.

38. The formulation of claim 11, which has a total weight from about 250 mg to about 750 mg.

39. A pharmaceutical formulation according to claim 1, wherein the therapeutic agent is selected from the group consisting of beta-adrenergic agonists, anti-muscarinic agents, steroids, leukotriene antagonists and cromones, pharmaceutically acceptable salts thereof; and any therapeutically effective combinations thereof.

40. A pharmaceutical formulation according to claim 39, wherein the therapeutic agent is selected from the group consisting of salbutamol, salmeterol, formoterol, clenbuterol, ipratropium, glycotropium, tiotropium, oxytropium, beclomethasone, betamethasone, fluticasone, budesonide, montelukast, cromolyn sodium, nedocromil and pharmaceutically acceptable salts thereof and any therapeutically effective combinations thereof.

41. A pharmaceutical formulation as claimed in claim 28, wherein the one or more therapeutic agents having a systemic effect are absorbed through the skin in sufficient quantity to provide a therapeutic systemic effect.

42. The pharmaceutical formulation of claim 1, wherein the glycerides are glycerol esters of $C_8$-$C_{18}$ fatty acids or polyglycolysed glycerides.

43. The pharmaceutical formulation of claim 1, wherein said formulation is not bullet shaped and not conical shaped.

44. The pharmaceutical formulation of claim 1, wherein said formulation is spreadable at room temperature.

45. The pharmaceutical formulation of claim 1, wherein the therapeutic agent is selected from the group consisting of an androgen, an estrogen or a pharmaceutically acceptable salt thereof.

46. The pharmaceutical formulation of claim 1, wherein the therapeutic agent is testosterone or a pharmaceutically acceptable salt thereof.

* * * * *